United States Patent [19]

Mathiaparanam

[11] Patent Number: 4,970,308

[45] Date of Patent: Nov. 13, 1990

[54] DI(BIS-(INDOLYL)ETHYLENYL)TETRAHALOPHTALIDES

[75] Inventor: Ponnampalam Mathiaparanam, Appleton, Wis.

[73] Assignee: Appleton Papers Inc., Appleton, Wis.

[21] Appl. No.: 397,703

[22] Filed: Aug. 23, 1989

[51] Int. Cl.$^5$ .................. C07D 413/14; C07D 401/14; C07D 401/10; C07D 403/10

[52] U.S. Cl. ........................................ 544/80; 544/62; 544/143; 544/144; 546/187; 546/201; 548/456

[58] Field of Search .................. 544/62, 143, 144, 80; 546/187, 201; 548/456

[56] References Cited

U.S. PATENT DOCUMENTS 4,107,428 8/1978 Farber ................................ 548/456

4,349,679 9/1982 Garner et al. ....................... 548/456

4,812,569 3/1989 Eckstein ............................. 548/456

*Primary Examiner*—Cecilia Shen

*Attorney, Agent, or Firm*—Benjamin Mieliulis

[57] ABSTRACT

Chromogenic di-[bis-(indolyl)ethylenyl] tetrahalophthalides are disclosed of the formula

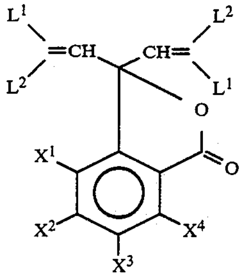

-continued wherein $L^1$ =

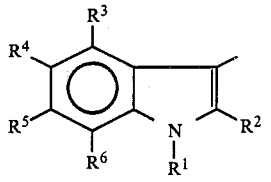

and $L^2$ =

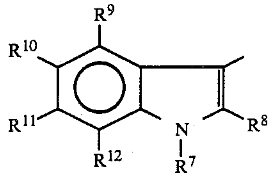

wherein each $X^1$, $X^2$, $X^3$, and $X^4$ is independently selected from chlorine or bromine;

wherein each of $R^1$ and $R^7$ is independently selected from cycloalkyl, aralkyl, alkoxyalkyl, or aroxyalkyl;

wherein each of $R^2$ and $R^8$ is independently selected from alkyl ($C_1$–$C_8$) or aryl (substituted or unsubstituted);

wherein each of $R^3$, $R^4$, $R^5$, $R^6$, $R^9$, $R^{10}$, $R^{11}$, and $R^{12}$ is independently selected from hydrogen, alkyl ($C_1$–$C_8$), cycloalkyl, aryl (substituted or unsubstituted), halogen, alkoxy ($C_1$–$C_8$), aroxy, cycloalkoxy, dialkylamino including symmetrical and unsymmetrical ($C_1$–$C_8$), alkylcycloalkylamino, dicycloalklamino, alkylarylamino,

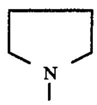 , 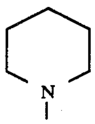 , 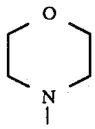 or 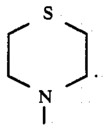 .

31 Claims, 4 Drawing Sheets

DI(BIS-(INDOLYL)ETHYLENYL)TETRAHALOPHTALIDES

FIELD OF INVENTION

1. Background of Invention

This invention relates to chromogenic di-[bis(indolyl-)ethylenyl]tetrahalophthalides and methods for their production. More particularly, this invention relates to chromogenic compounds which can give intense colors when reacted with an electron accepting coreactant material. More specifically, this invention relates to methods for the production of such chromogenic compounds for use in novel pressure-sensitive or heat-sensitive mark-forming record systems. As used in mark-forming systems, marking in desired areas on support webs or sheets may be accomplished by effecting localized reactive contact between the chromogenic material and the electron-accepting material on or in such web or sheet, such material being brought thereto by transfer or originally there in situ, the desired reactive contact forming colored images in the intended image marking areas.

2. Description of Related Art

Sheldon Farber, U.S. Pat. No. 4,119,776 issued Oct. 10, 1978, described vinyl phthalide color formers. Several divinyl phthalide chromogenic compounds (C1) [(C) $L^1$, $L^2$=substituted phenyl] (read as Compound C1 arrived at by referring to formula C wherein $L^1$ and $L^2$ are as stated) have been prepared by the condensation of ethylenes (A1) [(A) $L^1$, $L^2$=substituted phenyl] with phthalic anhydrides (B) [(B) Each Halogen is independently C1 or Br] in acetic anhydride.

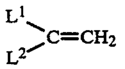
(A)

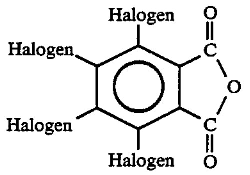
(B)

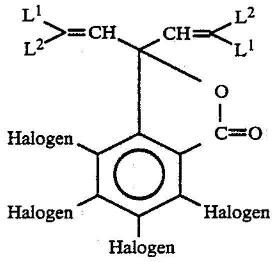
(C)

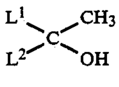
(D)

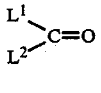
(E)

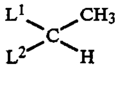
(F)

Substituted ethylenes (A1) or their precursors (D1) [(D) $L^1$,$L^2$=substituted phenyl] were prepared by the reaction of methylmagnesium bromide (also known as methyl Grignard reagent) with ketones (E1) [(E) $L^1$,$L^2$=substituted phenyl]. The use of Grignard reaction to prepare (A1) imposes severe restrictions on the scale up synthesis of (A1) and consequently on the manufacture of divinyl phthalides (C1).

In another synthetic approach, the alcohol (D1) was obtained by reacitng the ethan (F1) [(F) $L^1$, $L^2$=substituted phenyl] with lead peroxide in either nitric acid or formic acid; and the substituted ethylene (A1) was obtained from (D1) by dehydration ]Yamada Kagaku, Japan Kokai 1988-8360, filed June 30, 1986].

When indole was heated with acetic anhydride containing 10% acetic acid a bis(indolyl)ethylene (A2) [(A) $L^1$; , $L^2$=1-acetylindole-3-yl] was obtained as a by-product in 5-10% yield (J. E. Saxton, J. Chem. Soc., 3592 (1952)].

Substituted (2- and 1,2-) indoles when reacted with acetyl cyanide in the presence of hydrogen chloride yielded 1- cyano-1,1- di(3-indolyl)ethanes (G) and these products can be converted to bis(indolyl)ethylenes (H) by heating them under vacuum either alone or with soda lime. In some cases, depending on the substituents M and W, (G) yields (H) on refluxing with aqueous-ethanolic 10% potassium hydroxide [A. K. Kiang and F. G. Mann, J. Chem., Soc., 594 (1953)].

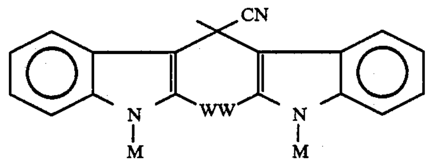
(G)

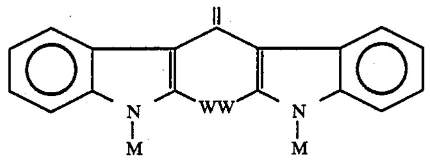
(H)

M = H, Ph
W = Me, Ph

Bis(indolyl)ethylene (H1) [(H) M=H and W=Me] was speculated to be a product (m.p. 203° C.) from the reaction of 2-methylindole with ethyl acetate and sodium ethoxide. No other data were given to substantiate the structure [A. Angeli and G. Marchetti, Atti. Accad. Lincei, 16 (II), 179 (1907)].

In another report (W. Borsche and H. Groth, Annalen, 549. 238 (1941)], 2-methylindole when boiled with acetyl chloride formed a product that on treatment with alkali gave a pseudobase, ($C_{20}H_{18}N_2$, pale rose, m.p. 208° C.). The pseudobase was suggested to be 1-(2-methylindole-3-yl)-1(2-methyl-3-indolidene)ethane (H2). Again, insufficient data precludes the substantiation of this structure. Furthermore, similar structure was proposed for the pseudobase obtained by substituting 2-phenylindole for 2-methylindole.

(H2)

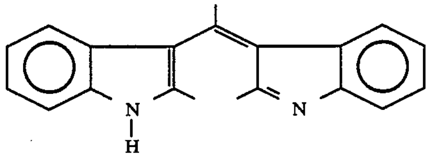

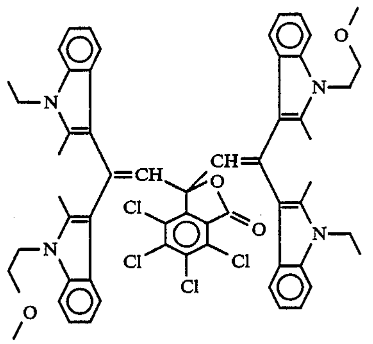

3,3-bis[1-(1-ethyl-2-methylindole-3-yl)-1-(1-β-methoxyethyl-2-methylindole-3-yl ]-4,5,6,7-tetrachlorophthalide.

Figure 1:
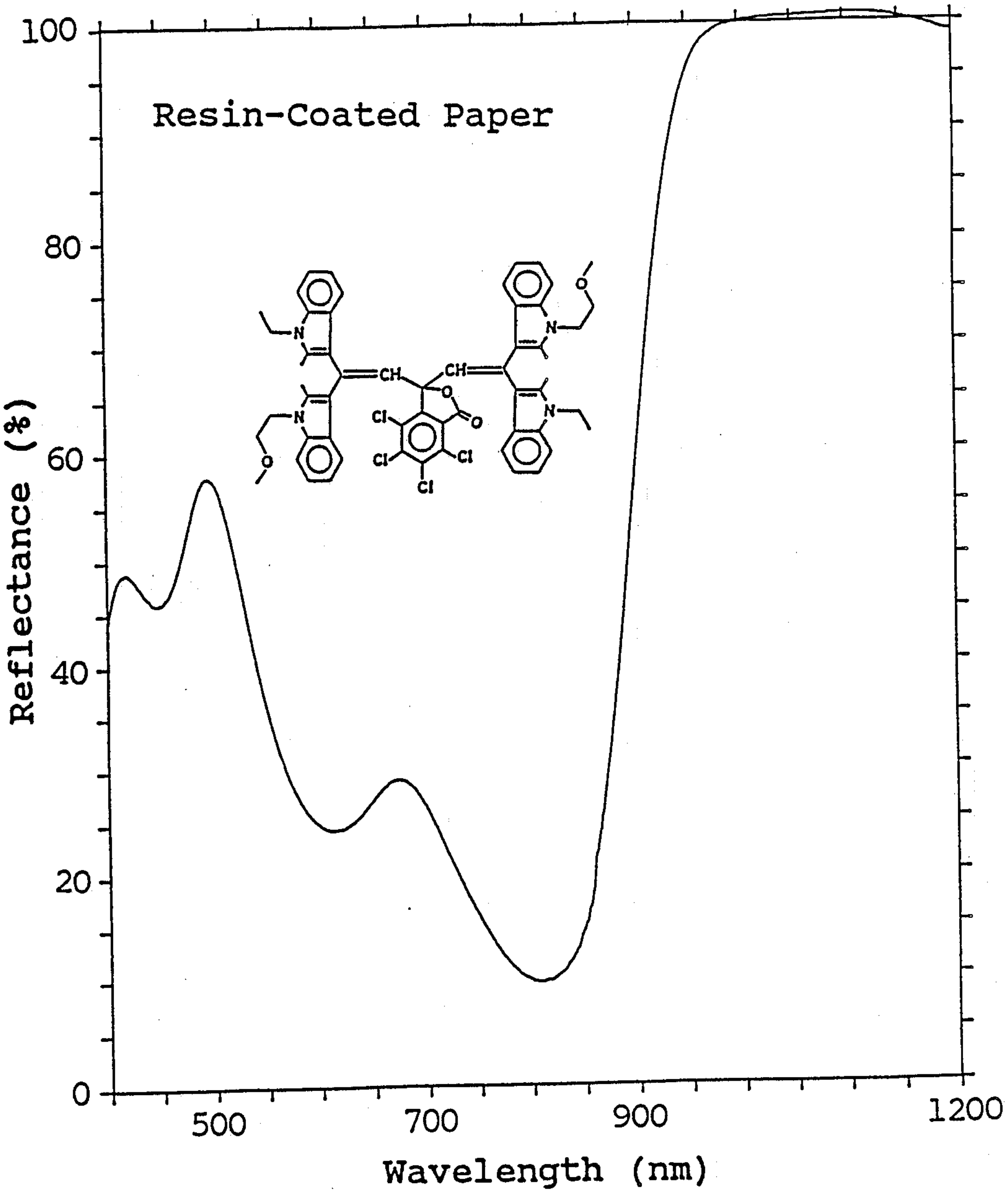
FIG. 1 is a graph of reflectance (%) from 400 to 1200 nm for the following compound when coated on resin-coated paper.
Figure 2:
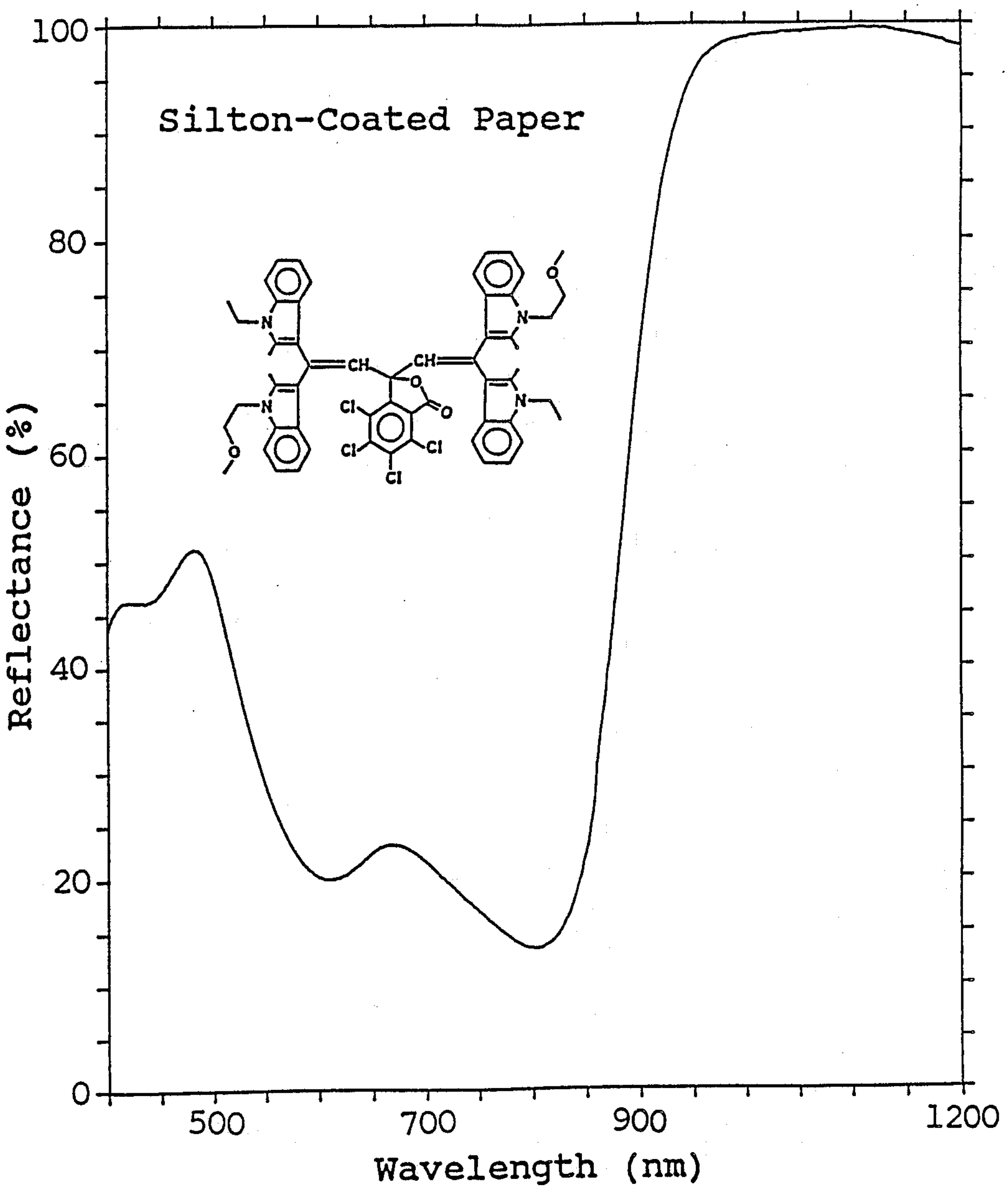

FIG. 2 is a graph of reflectance of the above compound when coated on silton-coated paper. Example 2 details the synthesis of this specific compound.

Figure 3:
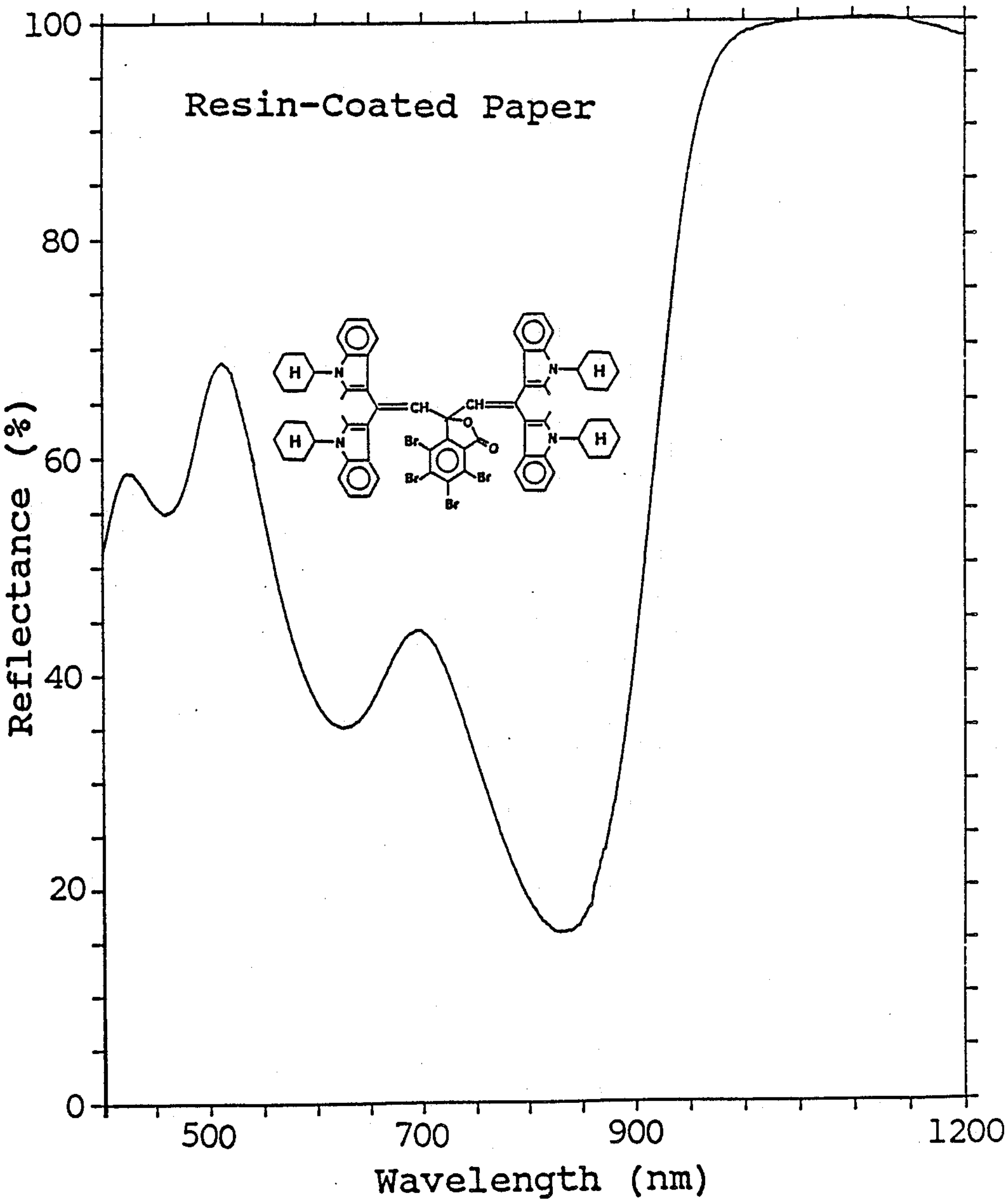

FIG. 3 is a graph of reflectance (%) from 400 to 1200 nm for the following compound when coated on resin-coated paper:

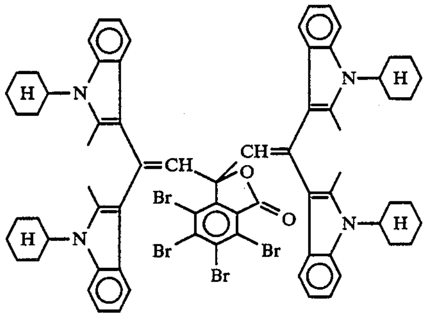

3,3-bis[1,1-bis(1-cyclohexyl-2-methylindole-3-yl)ethylene-2-yl]-4,5,6,7-tetrabromophthalide.

Figure 4:
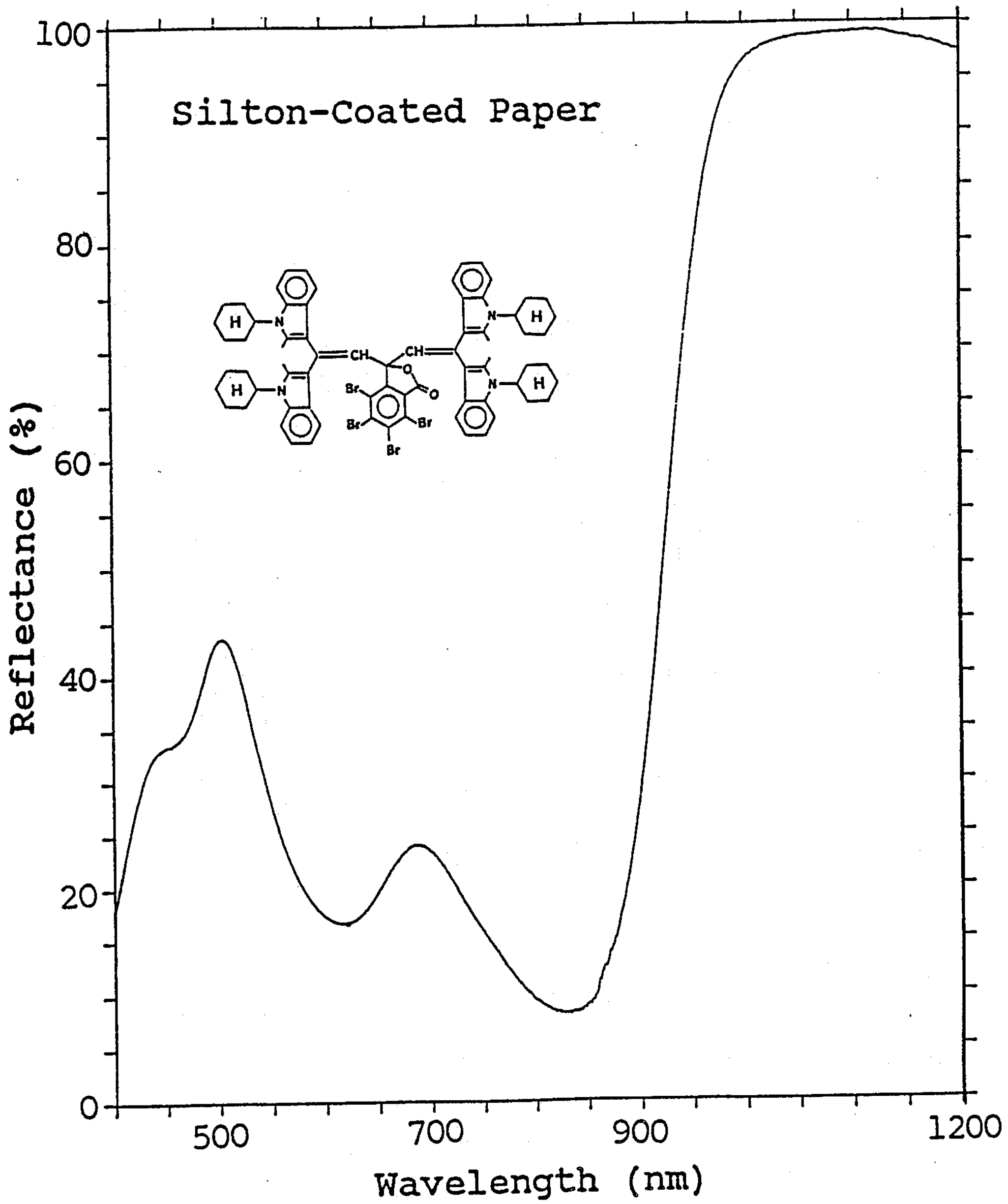

FIG. 4 is a graph of reflectance of the above compound when coated on silton-coated paper.

SUMMARY OF THE INVENTION

Novel symmetrical and unsymmetrical chromogenic di[bis-(indolyl)ethylenyl]tetrahalophthalides are disclosed. Specifically these compounds are chromogenic di-[bis(indolyl)ethylenyl]tetrahalophthalides of the formula

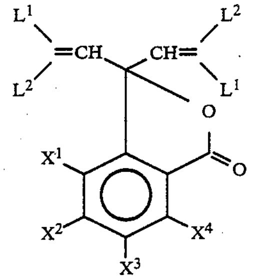

wherein $L^1$ =

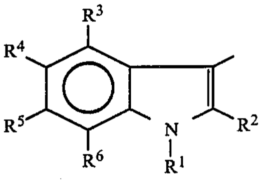

and $L^2$ =

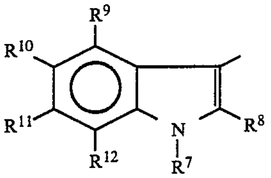

wherein each $X^1$, $X^2$, $X^3$, and $X^4$ is independently selected from chlorine or bromine;

wherein each of $R^1$ and $R^7$ is independently selected from cycloalkyl (e.g. cyclohexyl, cyclopentyl, cyclobutyl and cyclopropyl), aralkyl, alkoxyalkyl (e.g. β-methoxyethyl), aroxyalkyl (e.g. β-phenoxyethyl); wherein each of $R^2$ and $R^8$ is independently selected from alkyl ($C_1$–$C_8$) and aryl (substituted or unsubstituted);

wherein each of $R^3$, $R^4$, $R^5$, $R^6$,$R^9$, $R^{10}$, $R^{11}$, and $R^{12}$ is independently selected from hydrogen, halogen, alkyl ($C_1$–$C_8$), cycloalkyl, aryl (substituted or unsubstituted), halogen, alkoxy ($C_1$–$C_8$), aroxy, cycloalkoxy, dialkylamino including symmetrical and unsymmetrical alkyl ($C_1$–$C_8$), alkylcycloalkylamino, dicycloalkylamino, alkylarylamino,

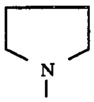 , 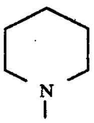 , 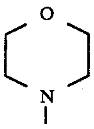 and 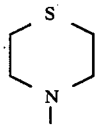 .

$J1 = L^1$ or $L^2$.

Novel methods are disclosed for producing these di-bis-(indolyl)ethylenyl]tetrahalophthalides. The above formula, for ease of reference, can also be expressed as (C2) [(C) wherein each Halogen is independently selected from chlorine or bromine; wherein each L namely, $L^1$ and $L^2$ is the same or different and is each independently selected from indole moieties (J1). This is read as new compound C2 arrived at by reference to formula C wherein $L^1$ and $L^2$ are as stated.

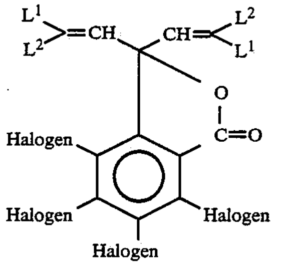
(C)

J1 = $L^1$ or $L^2$.

Preparation of di-[bis-(indolyl)ethylenyl]tetrahalophthalides (C2) comprises condensation of bis(indolyl-)ethylenes (A3) [(A) wherein each $L^1$ and $L^2$ is the same or different and is each independently selected from indole moieties (J1), with tetrahalophthalic anhydrides (B) in acetic anhydride with or without acetate of Group I or Group II elements of the periodic table.

The first route uses the corresponding indoles, acetic anhydride and Lewis acid such as zinc chloride or other electron acceptor preferably in approximately 1:1:0.5 molar ratios respectively in a suitable solvent. The second route uses the corresponding indoles with acetyl chloride preferably in approximately 1:(0.5–2.0) molar amounts at temperatures (15–75° C.) with or without solvent. The third route involves a condensation of component (K1) with indole (J1) in the presence of a Vilsmeier reagent (such as phosphoryl chloride, phosgene, oxalyl chloride, benzoyl chloride, alkanesulfonyl chloride, arenesulfonyl chloride, alkyl chloroformate and aryl chloroformate) with or without solvent. This third route can be used to conveniently prepare unsymmetrical indolyl ethylenes (i.e. (A3) with different $L^1$ and $L^2$).

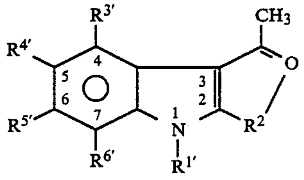
(K1)

wherein $R^{1'}$, $R^{2'}$, $R^{3'}$, $R^{4'}$, $R^{5'}$, $R^{6'}$of K1 are defined identically as $R^1$, Rhu 2, $R^3$, $R^4$, $R^5$ and $R^6$ respectively in formula $L^1$, i.e. $R^{1'}$is defined the same as $R^1$, $R^{2'}$is defined as $R^2$, $R^{3'}=R^3$, $R^{4'}=R^4$, $R^{5'}=R^5$ and $R^{6'}=R^6$.

The processes disclosed herein are versatile and can be used to prepared di[bis-(indolyl)ethylenyl]tetrahalophthalides using indoles with broader substitution patterns than simply J1, i.e., can be used to make compounds broader in scope than (C). In other words, if desired, in the disclosed processes, K1's substituents $R^{1'}$and $R^{2'}$can be broader than $R^1$ and/or $R^2$ of J1. Thus, $R^{1'}$can additionally, in the disclosed processes, include hydrogen, alkyl ($C_1$–$C_8$), substituted or unsubstituted aryl, and alkoxy. $R^{2'}$can additionally in the processes include hydrogen.

Solvents as referred to herein are preferably organic and more preferably the halogenated organic solvents such as 1,2-dichloroethane and chlorobenzene and the like.

Di-[bis-(indolyl)ethylenyl]tetrahalophthalides (C2) are prepared via two major routes from bis(indolyl-)ethylenes (A3) and tetrahalophthalic anhydrides (B). In the first route bis(indolyl)ethylene (A3) and tetrahalophthalic anhydride (B) in 2:1molar ratio respectively were heated at 100–110° C. in acetic anhydride for 2–3 hours. In the case of acid sensitive bis(indolyl-)ethylene, acetate of Group I or Group II elements was added to the above reaction mixture to improve the yield of (C2). In the second route, the bis(indolyl)ethylene (A3) is generated in situ from the indole (J1) and acetyl chloride with or without solvent and then condensed with tetrahalophthalic anhydride (B) in the presence of acetate of Group I or Group II elements and acetic anhydride at 100–110° C. for 2–3 hours. This procedure, referred to as one-pot two-step synthesis, has several advantages over the first route; for example, (a) it simplifies the process for the manufacture of di-[bis-(indolyl)ethylenyl]tetrahalophthalides (C2) by eliminating the isolation and purification of intermediate bis(indolyl)ethylenes; and (b) unstable or difficult to isolate bis(indolyl)ethylenes (A3) are condensed in situ with tetrahalophthalic anhydrides (B) to give (C2) that are difficult to prepare otherwise.

All the above-mentioned methods are conducive to scale-up and are used to prepare a variety of di-[bis-(indolyl)ethylenyl]tetrahalophthalides (C2). Some examples are illustrated in Table 1.

TABLE 1

| Entry | Compound | M.P. (°C.) | Color |
|---|---|---|---|
| 1. | 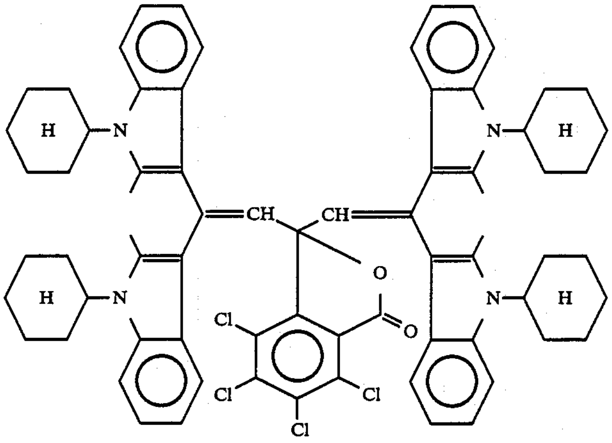 | 238–240 | Grey |

TABLE 1-continued
| Entry | Compound | M.P. (°C.) | Color |
|---|---|---|---|
| 2. | 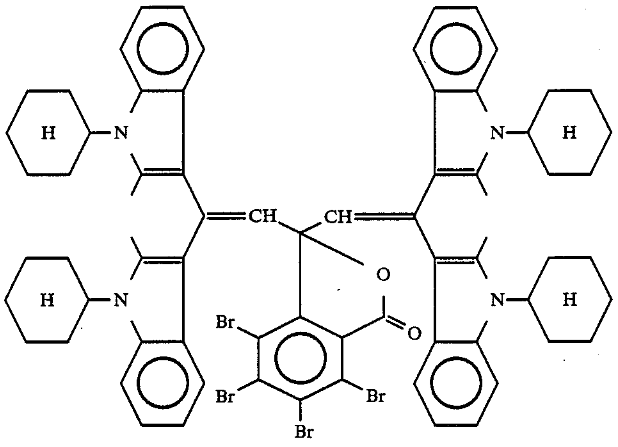 | 252–253 | Pale Yellow |
| 3. | 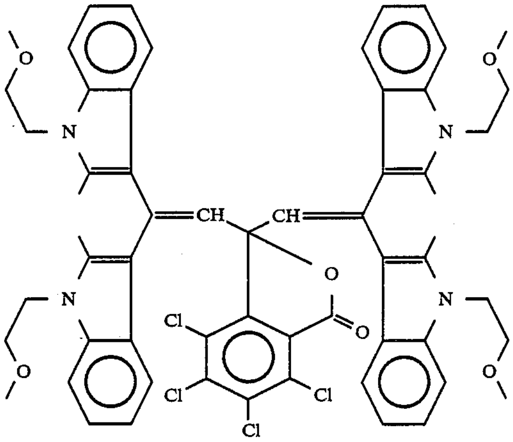 | 140–142 | Pale Yellow |
| 4. | 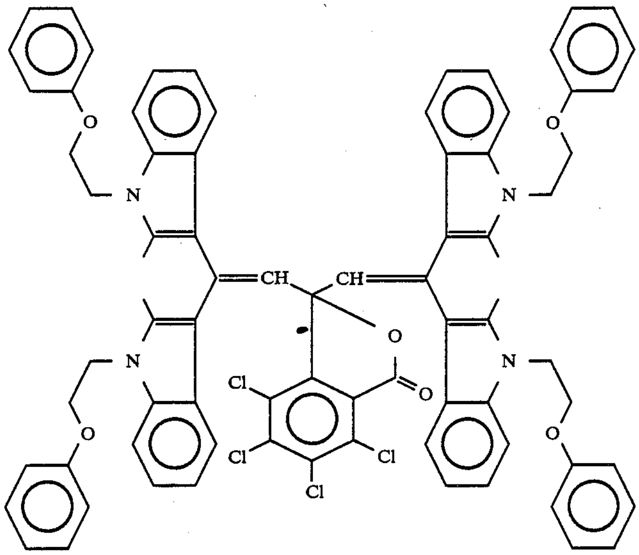 | 137–140 | Pale Yellow |

TABLE 1-continued
| Entry | Compound | M.P. (°C.) | Color |
|---|---|---|---|
| 5. | 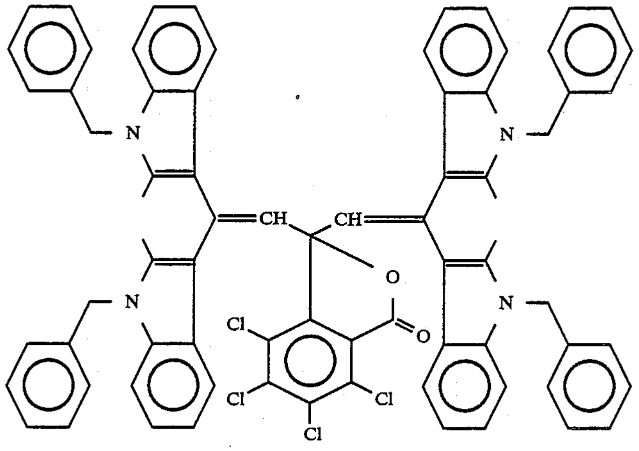 | 255-260 | Grey |
| 6. | 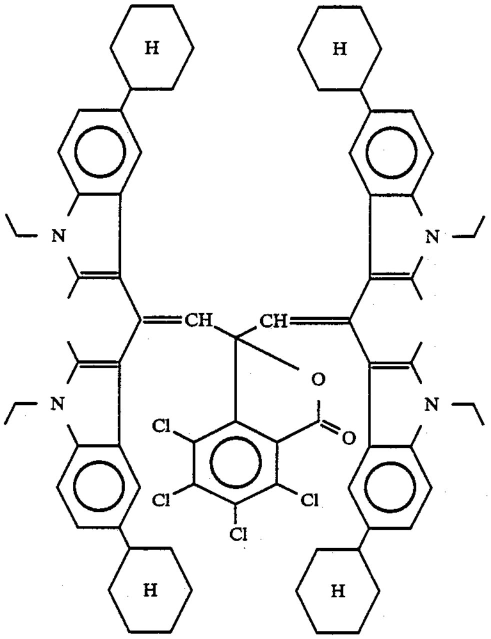 | 225-228 | Pale Yellow |
| 7. | 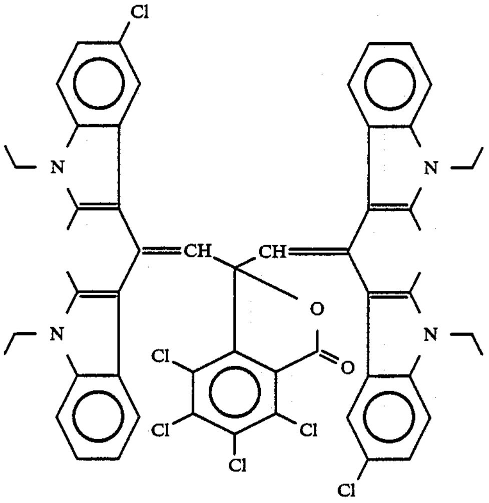 | 172-175 | White |

TABLE 1-continued

| Entry | Compound | M.P. (°C.) | Color |
|---|---|---|---|
| 8. | 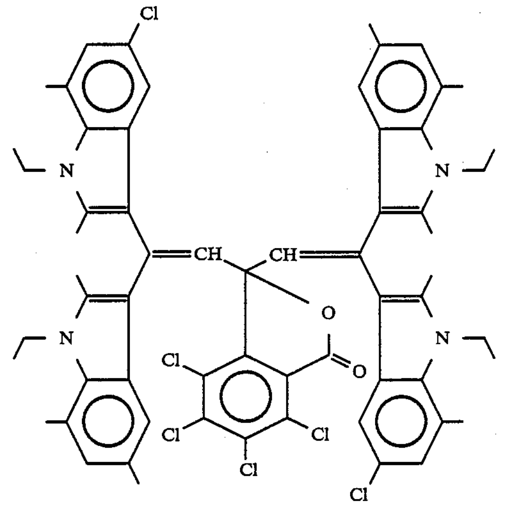 | 269–271 | White |
| 9. | 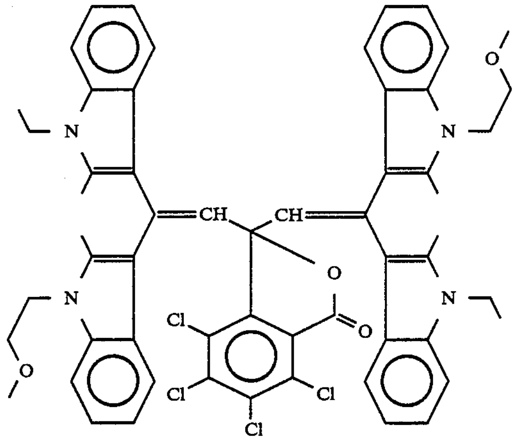 | 213–217 | Brown |

DETAILED DESCRIPTION

This invention teaches a process for the preparation of chromogenic compounds which in color form have absorbance in the infrared region of the spectrum at approximately 700–1200 nm and thus are eligible for use in pressure-sensitive and thermal recording systems. Compounds which are chromogenic and absorptive in the near infrared region of the spectrum have commercial utility by being capable, when imaged, of being detected by optical reading machines.

More particularly, this invention describes novel methods for the preparation of substantially colorless but colorable chromogenic compounds eligible for use in pressuresensitive recording and thermal recording systems. Advantageously recording systems utilizing these compounds can be read by optical reading machines, particularly those capable of reading for the infrared wavelength range of 700–200 nm.

The colorable chromogenic compounds of the invention, can be combined with other chromogenic materials covering other or wider spectral ranges and can be used in pressure-sensitive and thermal recording systems to provide images which absorb over wider ranges of the electromagnetic spectrum. The commercial significance is that a larger assortment of available optical readers can thus be effectively useful with such imaged record systems.

The chromogenic compounds of the invention also find use in photosensitive printing material, typewriter ribbons, inks and the like.

More specifically the process of the invention relates to the preparation of chromogenic compounds having two vinyl linkages. These compounds are substantially colorless or slightly colored solids but can be converted to colored forms upon reactive contact with an electron accepting material. The compounds of the invention in imaged or colored form are typically dark colored and are remarkably absorptive of near infrared light such that images formed of these compounds can be detected by conventional optical readers capable of detecting in the infrared wavelength range of 700–1200 nm.

In the invention di-[bis-(indolyl)ethylenyl]tetrahalophthalides (C2) [(C) wherein each halogen is independently selected from chlorine or bromine; wherein each L namely, $L^1$ and $L^2$ is the same or different and is each independently selected from indole moieties of the formulae (J1)] are prepared. (C2) is understood or read to be compound (C) as described in the brackets and with reference to the formula set forth below.

The processes described for the preparation of (C2) are very conducive to scale up.

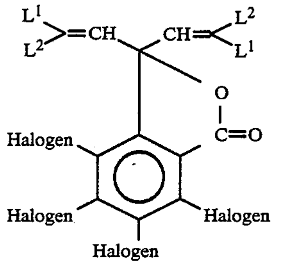

(C)

J1=$L^1$ or $L^2$ are as earlier defined herein. The halogen is each independently chlorine or bromine.

In forming pressure-sensitive or heat-sensitive mark-forming record systems with di-[bis-(indolyl)ethylenyl]-tetrahalophthalides of the invention, the eligible acidic, or electron acceptor materials include, but are not limited to, acid clay substances such as attapulgite, bentonite and montmorillonite and treated clays such as silton clay as disclosed in U.S. Pat. Nos. 3,622,364 and 3,753,761, phenols and diphenols as disclosed in U.S. Pat. No. 3,539,375, aromatic carboxylic acids such as salicylic acid, metal salts of aromatic carboxylic acids as disclosed in U.S. Pat. No. 4,022,936 and acidic polymeric material such as phenol-formaldehyde polymers as disclosed in U.S. Pat. No. 3,672,935 and oil-soluble metal salts of phenol-formaldehyde polymers as disclosed in U.S. Pat. No. 3,732,120. The compounds of this invention are useful as color formers in recording materials such as, for example, pressure-sensitive copying paper, thermally-responsive record material, electro heat-sensitive recording paper and thermal ink.

Pressure-sensitive copying paper systems provide a marking system and can be assembled by disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation, preferably comprises microcapsules containing liquid solvent solution. The microencapsulation process utilized can be chosen from the many known in the art. Well known methods are disclosed in U.S. Pat. Nos. 2,800,457; 3,041,289: 3,533,958; 3,755,190; 4,001,140 and 4,100,103. Any of these and other methods are suitable for encapsulating the liquid solvent containing the chromogenic compounds of this invention.

The chromogenic compounds of this invention are particularly useful in pressure-sensitive copying paper systems which incorporate a marking liquid comprising a vehicle in which is dissolved a complement of several colorless chromogenic compounds each exhibiting its own distinctive color on reaction with an eligible acidic record material sensitizing substance. Such marking liquids are disclosed in U.S. Pat. No. 3,525,630.

Thermally-responsive record material systems provide a marking system of color forming components which relies upon melting or subliming one or more of the components to achieve reactive, color-producing contact. The record material includes a substrate or support material which is generally in sheet form. Components of the color-forming system are in a substantially contiguous relationship, preferably substantially homogeneously distributed throughout a coated layer or layers of material deposited on the substrate. In manufacturing the record material, a coating composition is preferred which includes a fine dispersion of the components of the color-forming system, polymeric binder material, surface active agents and other additives in an aqueous coating medium.

The chromogenic compounds of this invention are useful in thermally-responsive record material systems either as single chromogenic compounds or in mixtures with other chromogenic compounds. Examples of such systems are given in U.S. Pat. Nos. 3,539,375 and 4,181,771.

Thermally-responsive record material systems are well known in the art and are described in many patents, for example U.S. Pat. Nos. 3,539,375; 3,674,535; 3,746,675; 4,151,748; 4,181,771; and 4,246,318 which are hereby incorporated by reference. In these systems, basic chromogenic material and acidic color developer material are contained in a coating on a substrate which, when heated to a suitable temperature, melts or softens to permit said materials to react, thereby producing a colored mark.

In the field of thermally-responsive record material, thermal sensitivity (response) is defined as the temperature at which a thermally responsive record material produces a colored image of satisfactory intensity (density). Background is defined as the amount of coloration of a thermally-responsive record material before imaging and/or in the unimaged areas of an imaged material. The ability to maintain the thermal sensitivity of a thermally-responsive record material while reducing the background coloration is a much sought after and very valuable feature.

One of the uses for thermally responsive record material which is enjoying increasing importance is facsimile reproduction. Alternative terms for facsimile are telecopying and remote copying. In the facsimile system, images transmitted electronically are reproduced as hard copy. One of the important requirements for thermally-responsive record material to be used in facsimile equipment is that it have good (low coloration) background properties.

Increases in the sensitivity of thermally-responsive record material have been achieved through the incorporation of a phenylhydroxynaphthoate compound or a hydroxyanilide compound in the color-forming composition along with the chromogenic material and developer material as disclosed in U.S. Pat. No. 4,470,057 or U.S. Pat. No. 4,535,347, respectively, by Kenneth D. Glanz. Such sensitizer materials can be advantageously used in combination with the present invention.

The record material includes a substrate or support material which is generally in sheet form. For purposes of this invention, sheets also mean webs, ribbons, tapes, belts, films, cards and the like. Sheets denote articles having two large surface dimensions and a comparatively small thickness dimension. The substrate or support material can be opaque, transparent or translucent and could, itself, be colored or not. The material can be fibrous including, for example, paper and filamentous synthetic materials. It can be a film including, for example, cellophane and synthetic polymeric sheets cast, extruded, or otherwise formed. The gist of this invention resides in the color-forming composition coated on the substrate. The kind or type of substrate material is not critical.

Although not required to practice and demonstrate the beneficial properties of the claimed invention, the inclusion of certain sensitizing materials in the color-forming system provides a further improvement in properties, especially increases in sensitivity. Materials such as 1,2-diphenoxyethane, N-acetoacetyl-o-toluidine, parabenzylbipbenyl; phenyl-1-hydroxy-2-naphthoate, stearamide and p-hydroxyoctadecanilide are useful as such sensitizing materials. A listing of additional sensitizers can be found in U.S. Pat. No. 4,531,140.

The components of the color-forming system are in a contiguous relationship, substantially homogeneously distributed throughout the color-forming system, preferably in the form of a coated layer deposited on the substrate. In manufacturing the record material, a coating composition is preferred which includes a fine dispersion of the components of the color-forming system, polymeric binder material, surface active agents and other additives in an aqueous coating medium. The composition can additionally contain inert pigments, such as clay, talc, aluminum hydroxide, calcined kaolin clay and calcium carbonate; synthetic pigments, such as urea-formaldehyde resin pigments; natural waxes such as carnauba wax; synthetic waxes; lubricants such as zinc stearate; wetting agents and defoamers.

The color-forming system components are substantially insoluble in the dispersion vehicle (preferably water) and are ground to an individual average particle size of between about 1 micron to about 10 microns, preferably about 1 to about 3 microns. The polymeric binder material is substantially vehicle soluble, although latexes are also eligible in some instances. Preferred water-soluble binders include polyvinyl alcohol, hydroxyethylcellulose, methylcellulose, hydroxypropylmethylcellulose, starch, modified starches, gelatin and the like. Eligible latex materials include polyacrylates, polyvinylacetates, polystyrene, and the like. The polymeric binder is used to protect the coated materials from brushing and handling forces occasioned by storage and use of the thermal sheets. Binder should be present in an amount to afford such protection and in an amount less than will interfere with achieving reactive contact between color-forming reactive materials.

Coating weights can effectively be about 3 to about 9 grams per square meter (gsm) and preferably about 5 to about 6 gsm. The practical amount of color-forming materials is controlled by economic considerations, functional I0 parameters and desired handling characteristics of the coated sheets.

DESCRIPTION OF THE PREFERRED EMBODIMENTS

In the following examples, general procedures for preparing certain di-[bis-(indolyl)ethylenyl]tetrahalophthalides of formula (C2) are described; and the examples are not intended to be exhaustive and the moieties, as previously defined, are all eligible for use in any combination in preparing the compounds. Unless otherwise noted, all measurements, percentages and parts are by weight and in the metric system.

Satisfactory spectroscopic data were obtained for new compounds synthesized.

EXAMPLE 1

One-pot two-step preparation of 3,3-bis[1,1-bis(1-β-methoxyethyl-2-methylindole-3-yl) ethylene-2-yl]-4,5,6,7-tetrachlorophthalide

[Table 1, Entry 3]

1-β-methoxyethyl-2-methylindole (19.0g,0.1 mole) was stirred with acetyl chloride (16.0g.0.2 mole) at room temperature for 5 hours. Sodium acetate (16.4g,0.2 mole), acetic anhydride (30 ml) and tetrachlorophthalic anhydride (7.2g,0.025 mole) were added to the reaction mixture and the reaction mixture was heated at 100° C. for two hours, cooled to room temperature, stirred with excess aqueous sodium hydroxide (10%) and toluene. After stirring for 30 minutes at 60° C., toluene layer was separated. washed twice with hot water, dried and concentrated. The residue was warmed with isopropanol and filtered. The product was purified by column chromatography on silica gel, followed by recrystallization from chloroform/isopropanol. Yield: 11.3g(43%), pale yellow solid, m.p.: 140–142° C.

A solution of the product gives a greenish blue color to paper coated with a phenolic resin, with reflectance minima at 607 and 815 nm; and a blue color to paper coated with silton clay, with reflectance minima at 610 and 808 nm.

The calculated analysis for $C_{60}H_{58}N_4O_6Cl_4$, the title compound, is C,67.16%; H,5.45%; N,5.22%; and C1.13.22%. Found on analysis: C,67.17%; H,5.44%; N,5.10%; and C1,13.19%.

EXAMPLE 2

Preparation of 3.3-bis[1-(1-ethyl-2-methylindole-3-yl)-1-(1-β-methoxyethyl-2-methylindole-3-yl)ethylene-2-yl]-4,5,6,7-tetrachlorophthalide

[Table 1, Entry 9)

1-(1-ethyl-2-methylindole-3-yl)-1-(1-β-methoxyethyl-2-methylindole-3-yl)ethylene (3.7g, 0.01 mole) and tetrachlorophthalic anhydride(1.5g,0.005 mole) in acetic anhydride(15 ml) were heated at 120° C. for two hours, cooled down to room temperature and treated with aqueous sodium hydroxide(100 ml,10%) and toluene (100 ml). After vigorous stirring for 30 minutes. The toluene layer was separated. washed with hot water, dried and concentrated under reduced pressure. The residue was purified by chromatography on silica gel. The product obtained was heated with methanol, allowed to cool to room temperature and filtered; and, this process was repeated twice. Yield: 2.6g(51%), brown powder, m.p.: 213–217° C.

A solution of the product gives a green color to paper coated with a phenolic resin, with reflectance minima at 612 and 808 nm; and bluish green color to paper coated with silton clay, with reflectance minima at 609 and 809 nm.

The calculated analysis for $C_{58}H_{54}N_4O_4C_{14}$, the title compound, is C,68.77%; H,5.37%; N.5.53%; and C1,14.00%. Found on analysis: C,68.44%; H,5.15%; N,5.30%; and C1,14.61%.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit and scope of the invention.

What is claimed is:

1. A chromogenic di-[bis-(indolyl)ethylenyl]tetrahalophthalide of the formula

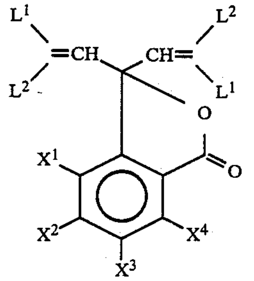

wherein $L^1$ =

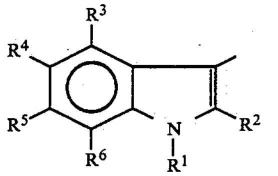

and $L^2$ =

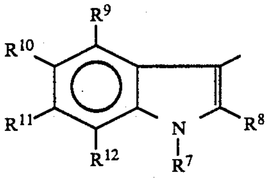

wherein each $X^1$, $X^2$, $X^3$ and $X^4$ is independently selected from chlorine or bromine;

wherein each of $R^1$ and $R^7$ is independently selected from cycloalkyl, aralkyl, alkoxyalkyl, or aroxyalkyl;

wherein each of $R^2$ and $R^8$ is independently selected from alkyl ($C_1$–$C_8$) or, aryl;

wherein each of $R^3$, $R^4$, $R^5$, $R^6$,$R^9$, $R^{10}$, $R^{11}$, and $R^{12}$ is independently selected from hydrogen, alkyl ($C_1$–$C_8$), cycloalkyl, aryl, halogen, alkoxy ($C_1$–$C_8$), aroxy, cycloalkoxy, dialkylamino including symmetrical and unsymmetrical alkyl ($C_1$–$C_8$), alkylcycloalkylamino, dicycloalkylamino, alkylarylamino,

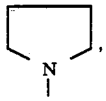, 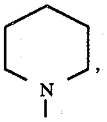, 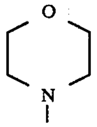 or 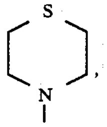, the alkyl moieties referred to herein being one to eight carbons, the cycloalkyl moieties referred to herein being three to six carbons.

2. The compound according to claim 1 wherein the di-[bis-(indolyl)ethylenyl]tetrahalophthalide is

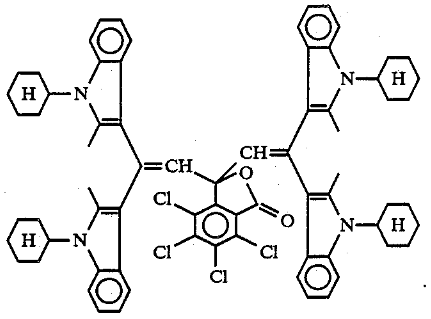

3. The compound according to claim 1 wherein the di-[bis-(indolyl)ethylenyl]tetrahalophthalide is

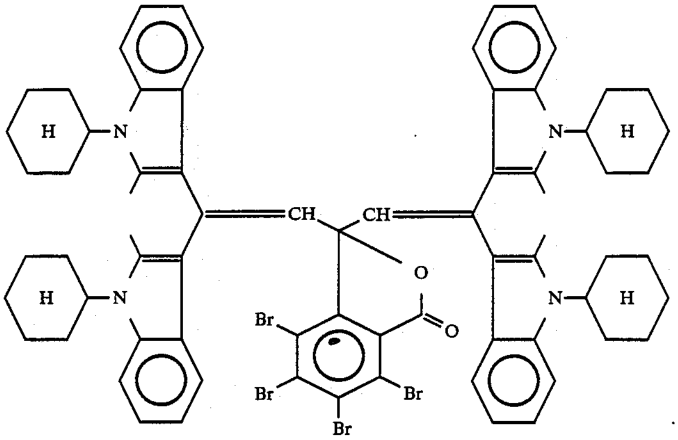

4. The compound according to claim 1 wherein the di-[bis(indolyl)ethylenyl]tetrahalophthalide is

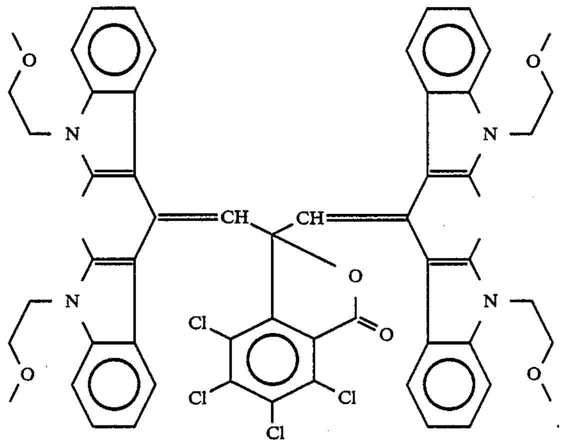
5. The compound according to claim 1 wherein the di-[bis(indolyl)ethylenyl]tetrahalophthalide is
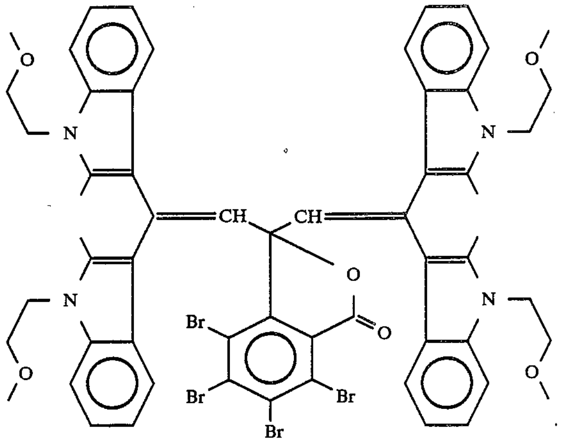
6. The compound according to claim 1 wherein the di-[bis(indolyl)ethylenyl]tetrahalophthalide is
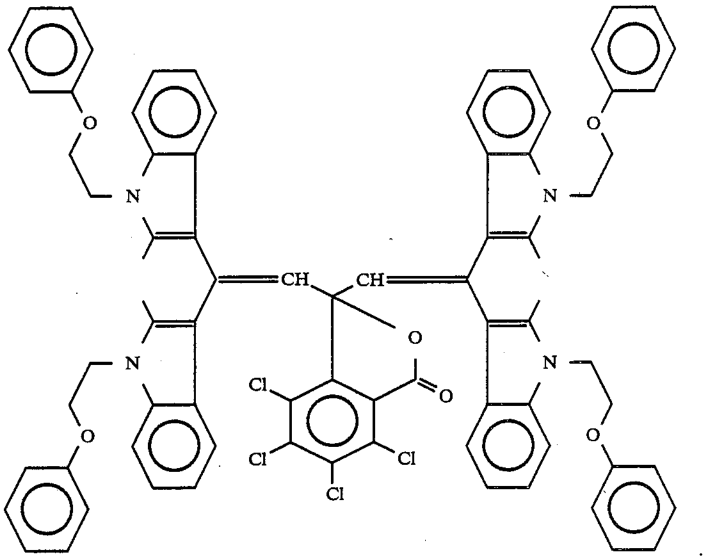
7. The compound according to claim 1 wherein the di-[bis(indolyl)ethylenyl]tetrahalophthalide is
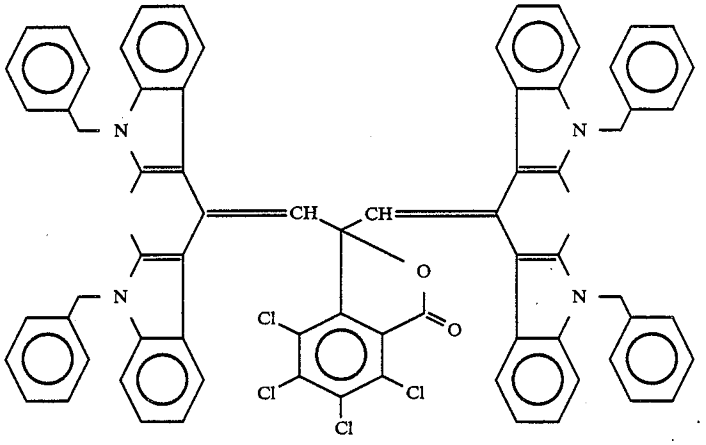

8. The chromogenic di-[bis(indolyl)ethylenyl]tetrahalophthalide according to claim 1 wherein each of $R^2$, and $R^8$ is alkyl and wherein each of $R^3$, $R^4$, $R^5$, $R^6$, $R^9$, $R^{10}$, $R^{11}$, and $R^{12}$ is hydrogen.

9. A chromogenic di-[bis(indolyl)ethylenyl]tetrahalophthalide of the formula

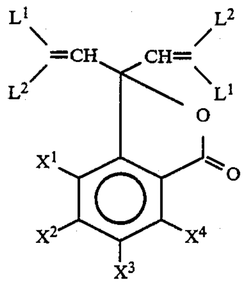

wherein $L^1$ =

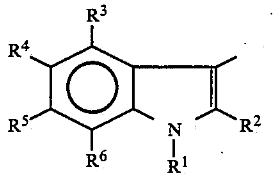

and $L^2$ =

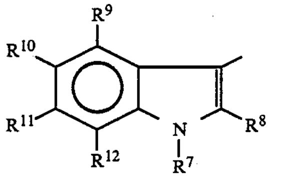

wherein each $X^1$, $X^2$, $X^3$ and $X^4$ is independently selected from chlorine or bromine;

wherein when at least one of $R^3$, $R^4$, $R^5$, $R^6$,$R^9$, $R^{10}$, $R^{11}$, and $R^{12}$ is cycloalkyl, alkylarylamino,

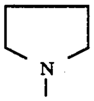, 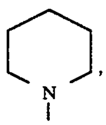, 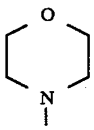 or 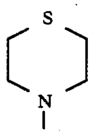

the balance of $R^3$, $R^4$, $R^5$, $R^6$,$R^9$, $R^{10}$, $R^{11}$, and $R^{12}$ is independently selected from hydrogen alkyl ($C_1$-$C_8$), cycloalkyl, aryl, halogen, alkoxy ($C_1$-$C_8$), aroxy, cycloalkyoxy, dialkylamino having symmetrical and unsymmetrical alkyl ($C_1$-$C_8$), alkylcycloalkylamino, dicycloalkylamino, or alkylarylamino, wherein each of $R^1$, $R^2$, $R^7$ and $R^8$ is independently selected from alkyl ($C_1$-$C_8$) or, aryl, the alkyl moieties referred to herein being from one to eight carbons, the cycloalkyl group referred to herein being from three to six carbons.

10. The compound according to claim 9 wherein the di-[bis(indolyl)ethylenyl]tetrahalophthalide is

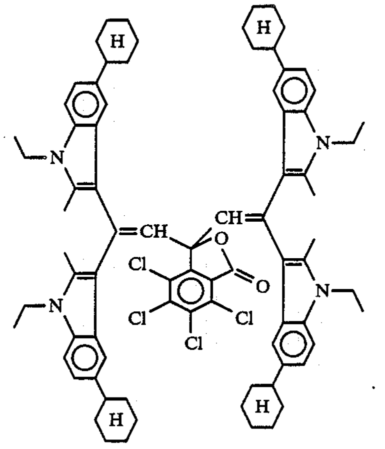

11. The compound according to claim 9 wherein the di-[bis(indolyl)ethylenyl]tetrahalophthalide is

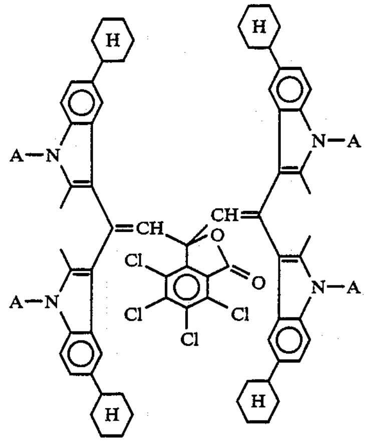

wherein A is $C_1$-$C_8$ alkyl.

12. The compound according to claim 9 wherein the di-[bis(indolyl)ethylenyl]tetrahalophthalide is

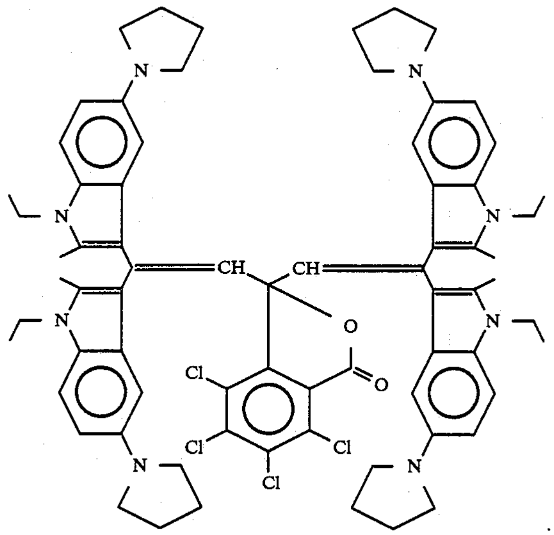

13. The compound according to claim 9 wherein the di-[bis(indolyl)ethylenyl]tetrahalophthalide is

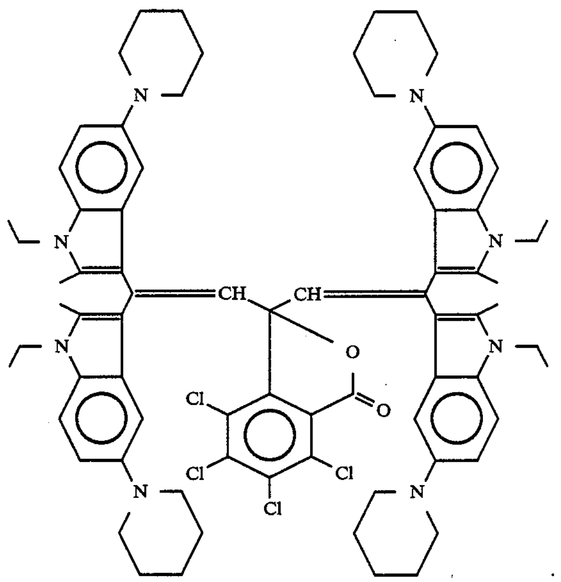

14. The compound according to claim 9 wherein the di-[bis(indolyl)ethylenyl]tetrahalophthalide is

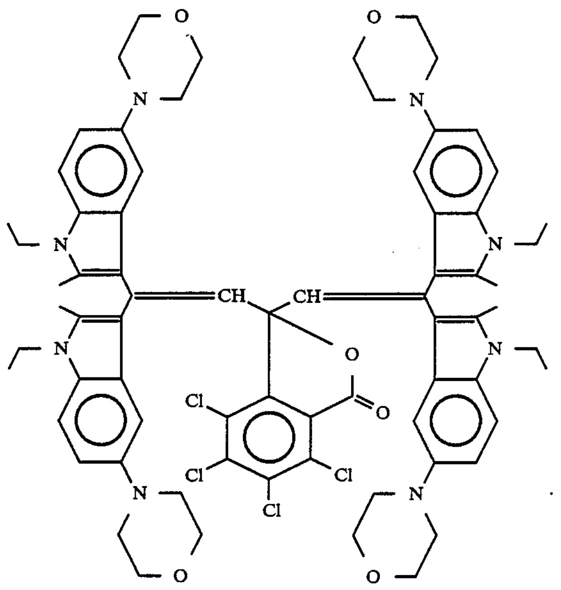

15. The compound according to claim 9 wherein the di-[bis(indolyl)ethylenyl]tetrahalophthalide is

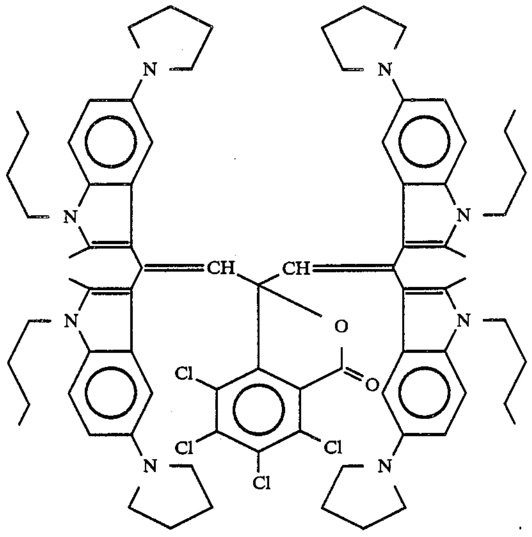

16. The compound according to claim 9 wherein the di-[bis(indolyl)ethylenyl]tetrahalophthalide is

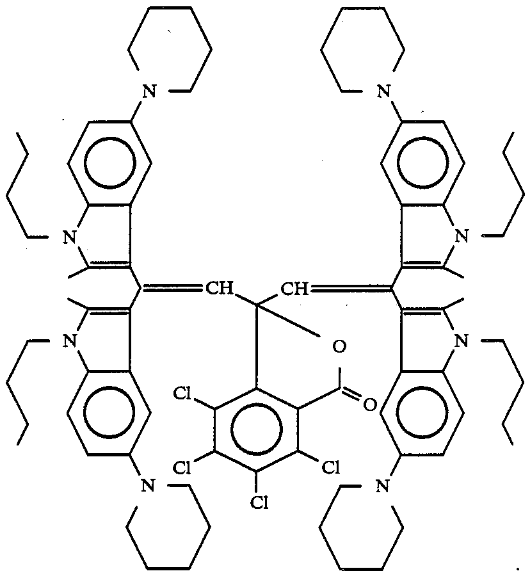

17. The compound according to claim 9 wherein the di-[bis(indolyl)ethylenyl]tetrahalophthalide is

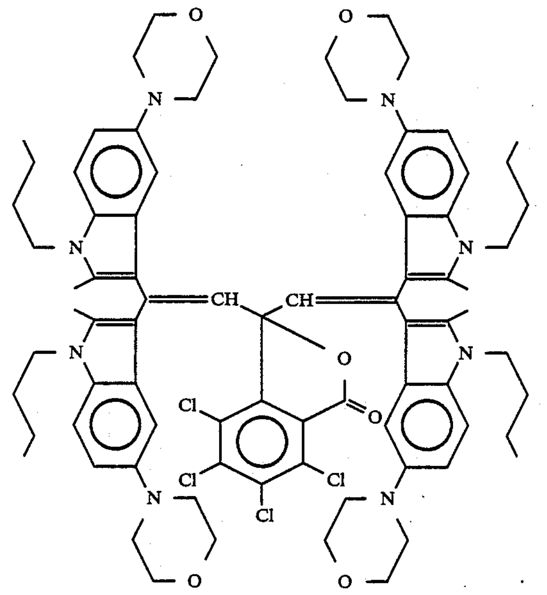

18. An unsymmetrical chromogenic di-[bis-(indolyl-)ethylenyl]tetrahalophthalide of the formula

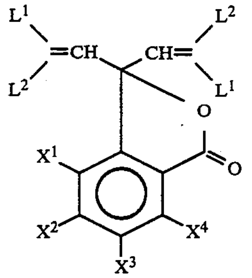

wherein indole moieties $L^1$ and $L^2$ are $L^1$ =

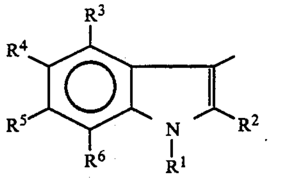

and $L^2$ =

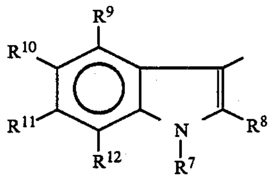

wherein each $X^1$, $X^2$, $X^3$, and $X^4$ is independently selected from chlorine or bromine;

wherein each of $R^1$ and $R^7$ is independently selected from alkyl ($C_1$–$C_8$), aryl, cycloalkyl, alkoxyalkyl or aroxyalkyl;

wherein each of $R^2$ and $R^8$ is independently selected from alkyl ($C_1$–$C_8$) or, aryl, wherein each of $R^3$, $R^4$, $R^5$, $R^6$,$R^9$, $R^{10}$, $R^{11}$, and $R^{12}$ is independently selected from hydrogen, halogen, alkyl ($C_1$–$C_8$), cycloalkyl, aryl, halogen, alkoxy ($C_1$–$C_8$), aroxy, cycloalkoxy, dialkylamino including symmetrical and unsymmetrical alkyl ($C_1$–$C_8$), alkylcycloalkylamino, dicycloalkylamino, alkylarylamino,

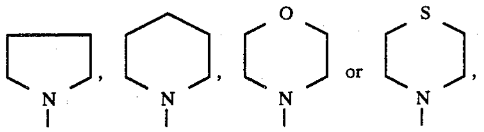

wherein each $L^1$ is the same or different;

wherein each $L^2$ is the same or different with the proviso however that at least one $L^1$ is not identical to at least one $L^2$, the alkyl moieties referred to herein being from one to eight carbons, the cycloalkyl groups referred to herein being from three to six carbons.

19. The compound according to claim 18 wherein unsymmetrical chromogenic di-[bis-(indolyl)ethylenyl]-tetrahalophthalide is

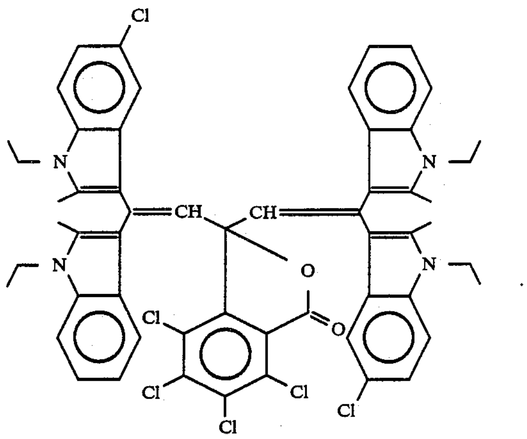

20. The compound according to claim 18 wherein unsymmetrical chromogenic di-[bis-(indolyl)ethylenyl]-tetrahalophthalide is

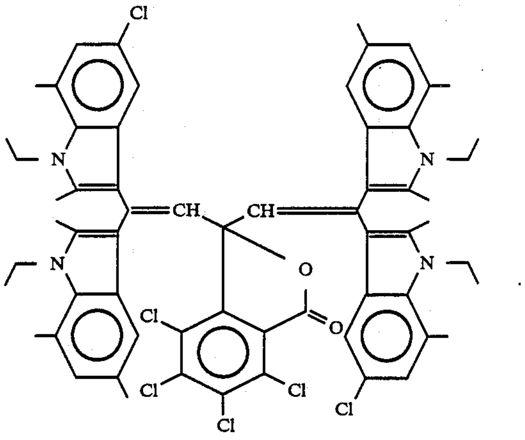

21. The compound according to claim 18 wherein unsymmetrical chromogenic di-[bis-(indolyl)ethylenyl]-tetrahalophthalide is

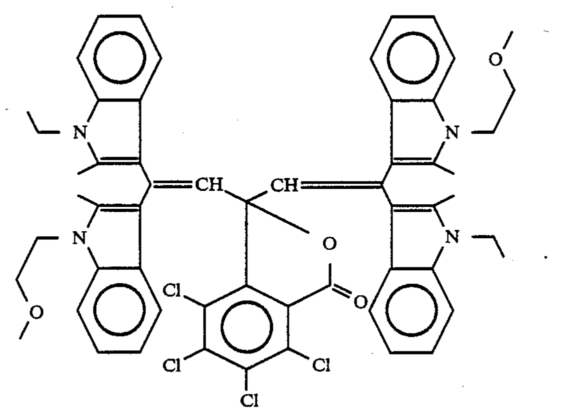

22. The compound according to claim 18 wherein unsymmetrical chromogenic di-[bis-(indolyl)ethylenyl]-tetrahalophthalide is

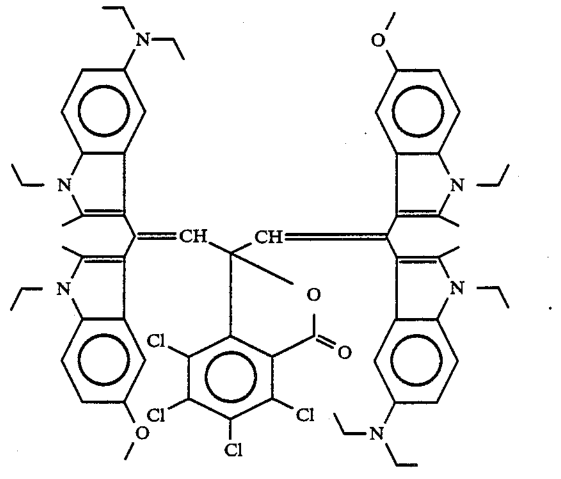

23. The compound according to claim 18 wherein unsymmetrical chromogenic di-[bis-(indolyl)ethylenyl]-tetrahalophthalide is

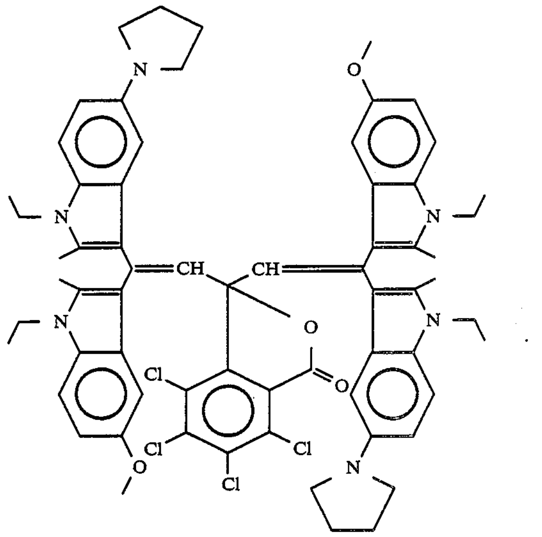

24. The compound according to claim 18 wherein unsymmetrical chromogenic di-[bis-(indolyl)ethylenyl]-tetrahalophthalide is

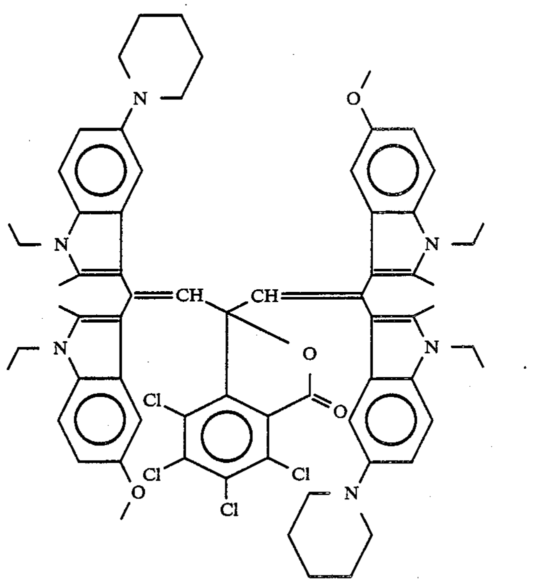

25. The compound according to claim 18 wherein unsymmetrical chromogenic di-[bis-(indolyl)ethylenyl]-tetrahalophthalide is

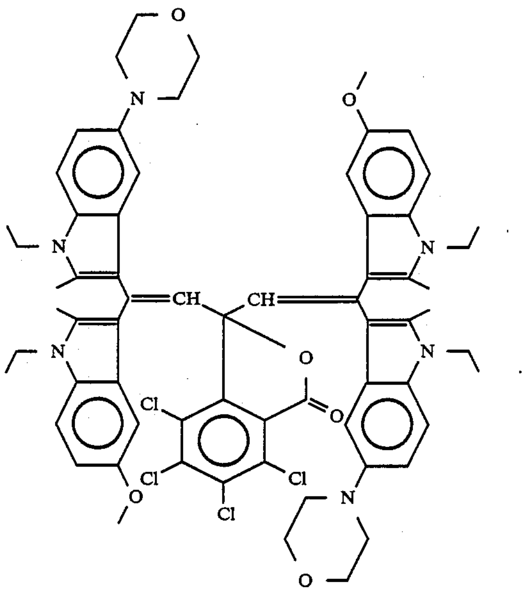

26. The compound according to claim 18 wherein unsymmetrical chromogenic di-[bis-(indolyl)ethylenyl]-tetrahalophthalide is

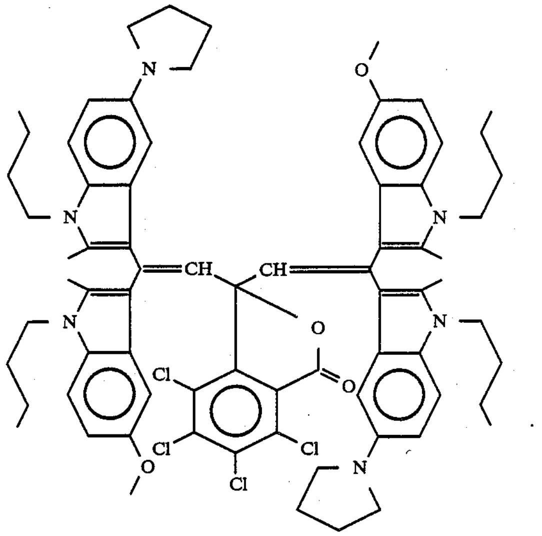

27. The compound according to claim 18 wherein unsymmetrical chromogenic di-[bis-(indolyl)ethylenyl]-tetrahalophthalide is

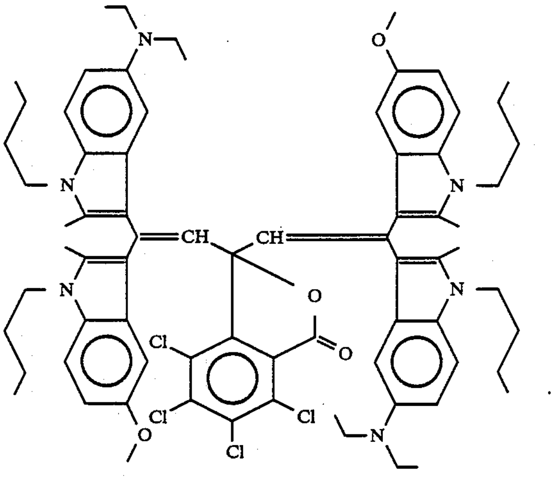

28. The compound according to claim 18 wherein unsymmetrical chromogenic di-[bis-(indolyl)ethylenyl]-tetrahalophthalide is

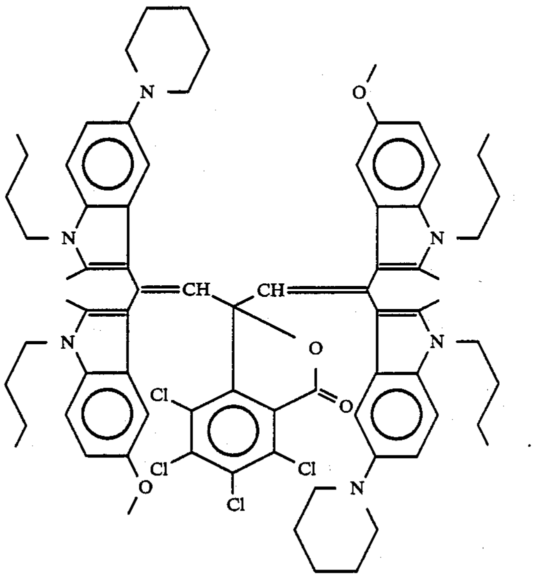

29. The compound according to claim 18 wherein unsymmetrical chromogenic di-[bis-(indolyl)ethylenyl]-tetrahalophthalide is

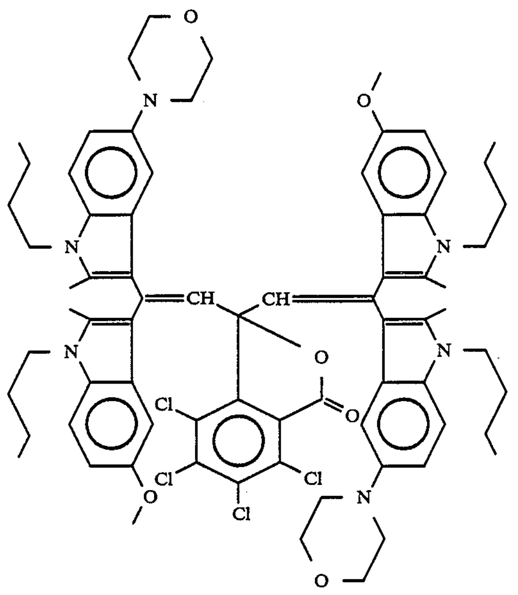

30. The chromogenic di-[bis(indolyl)ethylenyl]tetrahalophthalide according to claim 18 wherein each $R^1$ and $R^7$ independently is alkyl or alkoxyalkyl;

wherein each $R^2$ and $R^8$ independently is alkyl;

wherein each of $R^3$, $R^4$, $R^5$, $R^6$, $R^9$, $R^{10}$, $R^{11}$, and $R^{12}$ is independently selected from hydrogen, alkoxy, dialkylamino,

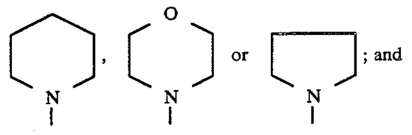

wherein at lest $L^1$ is not identical to at least one $L^2$, the alkyl moieties being from one to eight carbons.

31. The chromogenic di-[bis(indolyl)ethylenyl]tetrahalophthalide according to claim 18 wherein each $R^1$ and $R^7$ independently is alkyl or alkoxyalkyl;

wherein each $R^2$ and $R^8$ independently is alkyl;

wherein each of $R^3$, $R^4$, $R^5$, $R^6$, $R^9$, $R^{10}$, $R^{11}$, and $R^{12}$ is independently selected from hydrogen, alkyl, or halogen;

wherein at least one $L^1$ is not identical to at least one $L^2$, the alkyl moieties referred to herein being from one to eight carbons.

* * * * *

UNITED STATES PATENT AND TRADEMARK OFFICE
CERTIFICATE OF CORRECTION

PATENT NO. : 4,970,308

DATED : November 13, 1990

INVENTOR(S) : Mathiaparanam

It is certified that error appears in the above-identified patent and that said Letters Patent is hereby corrected as shown below:

On title page, Column 1 in the Title. The title should read DI(BIS-(INDOLYL)ETHYLENYL)TETRAHALOPHTHALIDES.

Column 2, line 10. Replace "reacitng the ethan" with --reacting the ethane--.

Column 2, line 13. The left bracket of "]Yamada" should be replaced by a right bracket --[Yamada--.

Column 3, line 33. In the space between "yl" and "]-4,5,6,7-tetra-" should be inserted --)ethylene-2-yl--.

Column 5, line 40-45. Correct the formula for (K1) to read

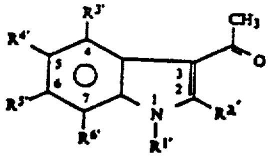

UNITED STATES PATENT AND TRADEMARK OFFICE
CERTIFICATE OF CORRECTION

PATENT NO. : 4,970,308

DATED : November 13, 1990

INVENTOR(S) : Eethhiaparanam

It is certified that error appears in the above-identified patent and that said Letters Patent is hereby corrected as shown below:

Column 6, line 2. Replace "Rhu$^2$" with --$R^2$--.

Column 11, line 57. "pressuresensitive" should read --pressure-sensitive--.

Column 15, line 54. Delete "IO" between "functional" and "parameters".

Column 21, line 54. In Claim 9, "cycloalkyoxy" should read --cycloalkoxy--.

Signed and Sealed this

Fifth Day of January, 1993

*Attest:*

DOUGLAS B. COMER

*Attesting Officer*

*Acting Commissioner of Patents and Trademarks*